United States Patent [19]

LaPointe et al.

[11] Patent Number: 5,189,192

[45] Date of Patent: Feb. 23, 1993

[54] PROCESS FOR PREPARING ADDITION POLYMERIZATION CATALYSTS VIA METAL CENTER OXIDATION

[75] Inventors: Robert E. LaPointe; Robert K. Rosen; Peter N. Nickias, all of Midland, Mich.

[73] Assignee: The Dow Chemical Company, Midland, Mich.

[21] Appl. No.: 642,111

[22] Filed: Jan. 16, 1991

[51] Int. Cl.$^5$ .................... C07C 7/00; C07C 9/00; C07C 11/00; C07C 13/00; C07C 15/00

[52] U.S. Cl. .................................... 556/11; 556/1; 556/7; 556/9; 556/13; 556/14; 556/27; 556/32; 556/50; 556/81; 556/110; 556/143

[58] Field of Search ............... 556/436, 51, 28, 11, 556/1, 9, 13, 7, 14, 32, 50, 81, 110, 143

[56] References Cited

U.S. PATENT DOCUMENTS 4,999,443  3/1991  Bertleff et al. ............... 556/28 X

OTHER PUBLICATIONS

Polyhedron 8, 1838–1843 (1989).
Organometallics 8, 2892–2903 (1989).
J. Am. Chem. Soc. 100:26, 8068–8073 (1978).
J. Chem. Soc. Chem. Comm. 1470–1471 (1990).
Gulf News, Sep. 12, 1990.
Gulf News, Sep. 13, 1990.

Primary Examiner—Arthur C. Prescott

[57] ABSTRACT

Addition polymerization catalysts comprising a derivative of a Group 4-8 metal compound prepared by metal center oxidation.

10 Claims, No Drawings

PROCESS FOR PREPARING ADDITION POLYMERIZATION CATALYSTS VIA METAL CENTER OXIDATION

BACKGROUND OF THE INVENTION

This invention relates to a process for preparing certain catalytically active metal complexes. More particularly, this invention relates to such a process involving oxidation of the metal center of a complex to form active catalyst compositions useful for polymerizing olefins, diolefins and/or acetylenically unsaturated monomers.

The use of Ziegler-Natta type catalysts in the polymerization of addition polymerizable monomers is, of course, well known in the prior art. In general, these soluble systems comprise a Group 4 or Lanthanide metal compound and a metal alkyl cocatalyst, particularly an aluminum alkyl cocatalyst. Several preparations for homogeneous olefin polymerization catalysts are known. These involve reacting a transition metal chloride with an aluminum alkyl, reacting a transition metal alkyl and a aluminum alkyl, reacting a transition metal alkyl with a proton source, or reacting a transition metal alkyl with a molecular oxidant. In these examples the oxidation state of the transition metal remains unchanged or may actually be reduced.

In *Polyhedron*, 8(13-14), 1838-1843 (1989), M. Bochmann et al., disclosed an oxidative process for preparing bispentamethylcyclopentadienyltitanium methyl tetraphenylborate using silver tetraphenylborate oxidant in tetrahydrofuran solvent. The complex was inactive in the polymerization of ethylene.

In *J. Am. Ch. Soc.* 109, 4111-4113 (1987) there is disclosed a process for preparation of cationic zirconium (IV) benzyl complexes by one electron molecular oxidation of d° organometallic compounds in tetrahydrofuran or methylene chloride solvent.

In both of the foregoing processes the solvents employed interfered with the resulting complex and detrimentally affected the catalytic ability of the catalyst in subsequent olefin polymerizations. In addition the references employed an oxidizing agent containing tetraphenylborate counter ion. Such anions, it has now been discovered, interfere with the resulting complex and are unacceptable for use in a metal center oxidation process for preparing addition polymerization catalysts.

In pending application Ser. No. 545,403, filed Jul. 3, 1990, two of the present inventors and other coinventors disclosed certain novel constrained geometry complexes possessing unique catalytic properties. In pending application Ser. No. 547,718, filed Jul. 3, 1990 the remaining inventor of the present invention disclosed a unique oxidative activation procedure for preparing complexes useful as addition polymerization catalysts. For the disclosures contained therein the preceding pending applications are hereby incorporated by reference in their entireties.

The present invention lies in the discovery of a novel technique for preparing certain metal complexes involving both metal center oxidation and cation complex formation in a single step. By combining what previously required two separate steps utilizing separate reagents and recovery systems, an improved and greatly simplified catalyst preparation is provided.

In accordance with the present invention there is provided a process for the preparation of a catalyst useful for addition polymerizations corresponding to the formula:

$L_lMX_n{}^+A^-$, wherein:

L independently each occurrence is an anionic or nonanionic ligand or ligand system;

M is a metal of group 4-8 of the periodic table also having an oxidation state, M*, one less than the state of the metal in the catalyst;

X independently each occurrence is hydride; halide; or a group selected from alkyl, alkenyl, silyl, germyl, aryl, and combinations thereof having up to 20 carbon, silicon or germanium atoms, and oxygen, nitrogen, phosphorus or sulfur containing derivatives thereof;

l is an integer greater than or equal to 1;

n is an integer greater than or equal to 1, and the sum of l and n together is one less than the valence of M; and $A^-$ is a monovalent compatible noncoordinating anion, the steps of the process comprising contacting under conditions to form the catalyst a reduced metal derivative corresponding to the formula: $L_lM^*X_n$, wherein L, l, n, X, and M* are as previously defined with an oxidizing agent capable of oxidizing M* to M and which in reduced form is noninterfering with the resulting catalyst, said oxidizing agent comprising a cationic oxidizer and a compatible noncoordinating anion, $A^-$.

Preferably the oxidizing agent corresponds to the formula:

$$Ox^+A^- \qquad (I)$$

wherein:

$Ox^+$ is a cationic oxidizer capable of oxidizing M* to M; and $A^-$ is a compatible noncoordinating anion.

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The term "anionic or nonanionic ligand or ligand system" refers to any ancillary, electron donating or electron sharing moiety. Such ligands include anionic ligands and neutral donor ligands.

Illustrative but nonlimiting examples of suitable anionic ligands include: R, $-R'(OR')_mOR$, $(OR')_mOR$, $-PR_2$, $-SR$, $-OR$, $-NR_2$, hydride, and organometalloid radicals comprising a Group 14 element wherein each of the hydrocarbyl substituents contained in the organic portion of said organometalloid, independently, contain from 1 to 20 carbon atoms. In these ligands:

R is a hydrocarbyl, silyl, germyl or a substituted hydrocarbyl, silyl, or germyl group of from 1 to 50 carbon, silicon, or germanium atoms;

R' is $C_{2-10}$ alkylene, and m is an integer from zero to ten.

Preferred anionic ligands are cyclopentadiene; substituted cyclopentadiene; biscyclopentadiene; and bridged biscyclopentadiene groups such as methylene or silane bridged biscyclopentadiene ligands. A most preferred anionic ligand is a substituted cyclopentadiene group more full described hereafter.

Illustrative but non-limiting examples of suitable neutral donor ligands include: ROR, NR$_3$, PR$_3$, and SR$_2$ wherein R is as above defined.

The term "cationic oxidize" as used herein refers to an organic or inorganic ion having an oxidation potential sufficient to cause oxidation of the Group 4–8 metal center to the next higher oxidation state. Preferred cationic oxidizers have an oxidation potential of at least +0.20 volt and preferably at least +0.25 volt. Examples of suitable cationic oxidizers are ferrocenium and C$_{1-4}$ alkyl substituted ferrocenium ions, Ag$^+$, triphenylmethyl cation, azoamines, i.e. PhN=N(Ph)$_2$+, wherein Ph is phenyl, etc.

As used herein, the recitation "compatible noncoordinating anion" means an anion which when functioning as a charge balancing anion in the catalyst system of this invention does not transfer an anionic substituent or fragment thereof to any cationic species thereby forming a neutral metal product. "Compatible anions" are anions which are not degraded to neutrality during catalyst preparation or use. Examples of compatible noncoordinating anions are provided hereafter.

The recitation "metalloid", as used herein, includes nonmetals such as boron, phosphorus and the like which exhibit semi-metallic characteristics.

Preferred metals of Group 4–8 are titanium, zirconium, vanadium, chromium and iron. Especially preferred is titanium.

In the foregoing catalysts, X may include for example, hydride; halide (especially chloride); primary, secondary or tertiary alkyl; alkoxide; alkoxyalkyl; alkyl(polyalkyleneoxy)alkyl; dialkylaminoalkyl; dialkylaminoaralkyl; allyl; dialkylphosphinoalkyl; dialkylphosphinoaralkyl; etc. It has been found highly desirable when L is L', as explained hereafter, that X should be capable of stabilizing the resulting complex. In such case X preferably is allyl or amino, phosphino or alkoxy substituted hydrocarbyl of up to 20 carbons.

Preferred reduced metal derivatives for use herein correspond to the formula: L'M*X$_n$, wherein:
L' is a divalent derivative of a substituted cyclopentadienyl group imparting a constrained geometry to the metal active site and containing up to 50 non-hydrogen atoms;
M* is as previously defined;
X is an allyl group or an amino, phosphino or alkoxy substituted hydrocarbyl group of up to 20 carbons; and
n is one or two depending on the valence of M*.

By use of the term "constrained geometry" herein is meant that the metal atom is forced to greater exposure of the active metal site because of one or more substituents on the cyclopentadienyl or substituted cyclopentadienyl group forming a portion of a ring structure wherein the metal is both bonded to an adjacent covalent moiety and is held in association with the cyclopentadienyl or substituted cyclopentadienyl group through an $\eta^5$ bonding interaction. It is understood that each respective bond between the metal atom and the constituent atoms of the cyclopentadienyl or substituted cyclopentadienyl group need not be equivalent. That is the metal may be symmetrically or unsymmetrically π-bound to the cyclopentadienyl or substituted cyclopentadienyl group.

The geometry of the active metal site is further defined as follows. The center of the cyclopentadienyl or substituted cyclopentadienyl group may be defined as the average of the respective X, Y, and Z coordinates of the atomic centers forming the cyclopentadienyl or substituted cyclopentadienyl group. The angle, Θ, formed at the metal center between the center of the cyclopentadienyl or substituted cyclopentadienyl group and each other ligand of the metal complex may be easily calculated by standard techniques of single crystal X-ray diffraction. Each of these angles may increase or decrease depending on the molecular structure of the constrained geometry metal complex. Those complexes wherein one or more of the angles, Θ, is less than in a similar, comparative complex differing only in the fact that the constrain-inducing substituent is replaced by hydrogen have constrained geometry for purposes of the present invention. Preferably one or more of the above angles, Θ, decrease by at least 5% more preferably 7.5% compared to the comparative complex. Highly preferably, the average value of all bond angles, Θ, is also less than in the comparative complex.

Preferably, monocyclopentadienyl metal coordination complexes according to the present invention have constrained geometry such that the smallest angle, Θ, is less than 115°, more preferably less than 110°, most preferably less than 105°.

Highly preferred reduced metal derivative compounds are monocyclopentadienyl titanium compounds corresponding to the formula:

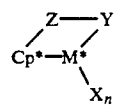

wherein:
M*, X, and n are as previously defined;
Cp* is a cyclopentadienyl or substituted cyclopentadienyl group bound in an $\eta^5$ bonding mode to M;
Z is a divalent moiety comprising oxygen, boron, or a member of group 14 of the periodic table of the elements; and
Y is a linking group comprising nitrogen, phosphorus, oxygen or sulfur or optionally Z and Y together form a fused ring system.

After metal center oxidation the catalysts correspond to the formula:

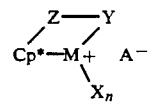

wherein Cp*, Z, M, X, n, and A$^-$ are as previously defined.

Each carbon atom in the cyclopentadienyl radical may be substituted or unsubstituted with the same or a different radical selected from the group consisting of hydrocarbyl radicals, substituted-hydrocarbyl radicals wherein one or more hydrogen atoms is replaced by a halogen atom, hydrocarbyl-substituted metalloid radicals wherein the metalloid is selected from Group 14 of the Periodic Table of the Elements, and halogen radicals. In addition two or more such substituents may together form a fused ring system. Suitable hydrocarbyl and substituted-hydrocarbyl radicals, which may be substituted for at least one hydrogen atom in the cyclopentadienyl radical, will contain from 1 to about 20 carbon atoms and include straight and branched alkyl radicals, cyclic hydrocarbon radicals, alkyl-substituted cyclic hydrocarbon radicals, aromatic radicals and alkyl-substituted aromatic radicals. Suitable organometalloid radicals include mono-, di- and tri-substituted organometalloid radicals of Group 14 elements wherein each of the hydrocarbyl groups contain from 1 to about 20 carbon atoms. More particularly, suitable organometalloid radicals include trimethylsilyl, triethylsilyl, ethyldimethylsilyl, methyldiethylsilyl, triphenylgermyl, trimethylgermyl and the like.

Most highly preferred reduced metal derivatives are amidosilane- or amidoalkanediyl- compounds corresponding to the formula:

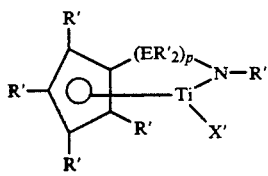

wherein:
R' each occurrence is independently selected from the group consisting of hydrogen, silyl, alkyl, aryl and combinations thereof having up to 10 carbon or silicon atoms;
E is silicon or carbon;
X' is allyl or dialkylaminoaralkyl of up to 10 carbons; and
p is 1 or 2.

Examples of the above most highly preferred metal coordination compounds include compounds wherein the R' on the amido group is methyl, ethyl, propyl, butyl, pentyl, hexyl, (including isomers), norbornyl, benzyl, phenyl, etc.; the cyclopentadienyl group is cyclopentadienyl, indenyl, tetrahydroindenyl, fluorenyl, octahydrofluorenyl, etc.; R' on the foregoing cyclopentadienyl groups each occurrence is hydrogen, methyl, ethyl, propyl, butyl, pentyl, hexyl, (including isomers), norbornyl, benzyl, phenyl, etc.; and X is methyl, neopentyl, trimethylsilyl, norbornyl, benzyl, methylbenzyl, phenyl, etc. Specific preferred reduced metal compounds include: (tert-butylamido) (tetramethyl-$\eta^5$-cyclopentadienyl)-1,2-ethanediyltitanium 2-(dimethylamino)benzyl, (tert-butylamido) (tetramethyl-$\eta^5$-cyclopentadienyl)-1,2-ethanediyltitanium 2-(dimethylamino)benzyl, (methylamido) (tetramethyl-$\eta^5$-cyclopentadienyl)-1,2-ethanediyltitanium allyl, (methylamido) (tetramethyl-$\eta^5$-cyclopentadienyl)-1,2-ethanediyltitanium 2-(dimethylphosphino)benzyl, (ethylamido) (tetramethyl-$\eta^5$-cyclopentadienyl)methylenetitanium 2-(diperfluorophenylamino)benzyl, (tert-butylamido)dibenzyl(tetramethyl-$\eta^5$-cyclopentadienyl)silanetitanium 2-(dimethylamino)benzyl, (benzylamido)diemthyl(tetramethyl-$\eta^5$-cyclopentadienyl)silanetitanium (dimethylaminomethyl)dimethylsily, (phenylphosphido)dimethyl(tetramethyl-$\eta^5$-cyclopentadienyl)silanetitanium 2-(dimethylamino)benzyl, and the like.

In the most preferred embodiment -Z-Y- is an amidosilane or amidoalkane group of up to 10 nonhydrogen atoms, i.e. (tert-butylamido)(dimethylsilyl), (tert-butylamido)-1-ethane-2-yl, etc.

Other reduced metal derivatives which are useful in the process of this invention, especially compounds containing other Group 4-8 metals will, of course, be apparent to those skilled in the art.

Compounds useful as oxidizing agents in the preparation of the compounds of this invention preferably comprise a cationic oxidizer, and one or more compatible noncoordinating anions, as previously explained.

In a preferred embodiment A⁻ of previous formula (I) comprises an anion which is a single coordination complex comprising a plurality of lipophilic radicals covalently coordinated to and shielding a central formally charge-bearing metal or metalloid atom, which anion is bulky and stable under the oxidation and subsequent polymerization conditions, and which anion is compatible with and noncoordinating towards the resulting Group 4-8 metal containing catalyst. The anion is employed only to provide charge balance without interfering with the oxidizing ability of Ox⁺ or the catalytic properties of the resulting catalyst. Any metal or metalloid capable of forming a coordination complex which is stable under the reaction conditions of the present invention may be contained in the anion. Suitable metals include, but are not limited to, aluminum, gold, platinum and the like. Suitable metalloids include, but are not limited to, boron, phosphorus, silicon and the like. Oxidizing agents containing anions comprising a coordination complex containing a single boron atom are most preferred.

Anions comprising boron which are particularly useful in the preparation of catalysts of this invention may be represented by the following general formula:

$$[BX_1X_2X_3X_4]^-$$

wherein:
B is boron in a valence state of 3;
$X_1$ to $X_4$ are the same or different nonreactive, organyl or silyl radicals containing from 6 to 20 carbon or silicon atoms. In addition two or more of $X_1$ to $X_4$ may be linked to each other through a stable bridging group. Preferably $X_1$ to $X_4$ lack reactive hydrogen moieties. That is, the radicals are either devoid of hydrogen, contain only hydrogen in nonactivated positions or contain sufficient steric hindrance to protect potentially active hydrogen sites. Examples of preferred radicals for $X_1$ to $X_4$ are perfluorinated hydrocarbyl radicals containing from 1 to 20 carbon atoms, 3,4,5-trifluorophenyl, 3,5-di(trifluoromethyl)phenyl, etc. It has now been discovered that one of $X_1$ to $X_4$ may be a $C_{1-10}$ organyl group, especially methyl or benzyl, without detrimentally affecting the inert properties of the anion.

A most highly preferred compatible, noncoordinating, anion is tetra(pentafluorophenyl)borate.

Suitable organic cationic oxidizers for use according to the present invention include ferrocenium ions, bisindenyl Fe(III) ions, and cationic derivatives of substituted ferrocene, and the like molecules, especially methyl substituted ferrocene. Suitable metal cationic oxidizers include $Ag^{+1}$, $Pd^{+2}$, $Pt^{+2}$, $Hg^{+2}$, $Hg_2^{+2}$, $Au^+$ and $Cu^+$. Most preferred cationic oxidizers are ferrocenium, substituted ferrocenium, and $Ag^{+1}$ cations.

Illustrative, but not limiting, examples of oxidizing agents in the preparation of the improved catalysts of this invention are ferrocenium tetra(pentafluorophenyl)borate, 1,1'-dimethylferrocenium tetrakis(perfluorophenyl) borate, gold (I) tetrakis 3,4,5-trifluorophenyl borate, silver tetra(pentafluorophenyl)borate, 1,1'-dimethylferrocenium tetrakis 3,5-bistrifluoromethylphenyl borate and the like.

Similar lists of suitable compounds containing other metals and metalloids which are useful as oxidizing agents (second components) could be made, but such lists are not deemed necessary to a complete disclosure. In this regard, it should be noted that the foregoing list is not intended to be exhaustive and other boron compounds that would be useful as well as useful compounds containing other metals or metalloids would be readily apparent, from the foregoing general equations, to those skilled in the art.

To recapitulate, it should be noted that the two compounds combined for preparation of the active catalyst must be selected so as to avoid transfer of a fragment of the anion, particularly an aryl group, to the metal cation, thereby forming a catalytically inactive species. This may be done by providing sufficient steric hindrance resulting from substituents on the groups attached to the Group 4-8 reduced metal derivative as well as substituents on the aromatic carbon atoms of the anion. It follows, then, that Group 4 and Lanthanide metal compounds (first components) comprising, e.g., perhydrocarbyl-substituted cyclopentadienyl radicals could be effectively used with a broader range of second components than could first components comprising less bulky radicals. As the amount and size of the metal substituents are reduced, however, more effective catalysts are obtained with second components containing anions which are more resistant to degradation, such as those with substituents on the meta and/or para positions of the phenyl rings. Another means of rendering the anion more resistant to degradation is afforded by fluorine substitution, especially perfluoro-substitution, in the anion. Second components containing fluoro-substituted stabilizing anions may, then, be used with a broader range of first components.

In general, the catalyst can be prepared by combining the first and second components in a suitable noninterfering, noncoordinating solvent at a temperature from $-100°$ C. to $300°$ C.

The catalyst may be used to polymerize $\alpha$-olefins and/or acetylenically unsaturated monomers having from 2 to about 18 carbon atoms and/or diolefins having from 4 to about 18 carbon atoms either alone or in combination. The catalyst may also be used to polymerize $\alpha$-olefins, diolefins and/or acetylenically unsaturated monomers in combination with other unsaturated monomers. In general, the polymerization may be accomplished at conditions well known in the prior art for Ziegler-Natta or Kaminsky-Sinn type polymerization reactions i.e. temperatures from $0°-250°$ C. and pressures from atmospheric to 1000 atmospheres. Suspension, solution, slurry or other process condition may be employed if desired. A support may be employed but preferably the catalysts are used in a homogeneous manner. It will, of course, be appreciated that the catalyst system will form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization mixture.

Suitable solvents for the formation of the catalyst are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

It is believed that the active catalyst species of the present invention contains a metal center which remains cationic and has a metal-carbon bond which is reactive with olefins, diolefins and acetylenically unsaturated compounds. Also associated with this metal center are one or more charge balancing anionic remnants of the formula $A^-$.

The catalyst formed by the method of this invention may be retained in solution or separated from the solvent, isolated, and stored for subsequent use. As previously indicated supra, the catalyst may also be prepared in situ during a polymerization reaction by passing the separate components into the polymerization vessel where the components will contact and react to produce the improved catalyst of this invention.

The equivalent ratio of reduced metal derivative to oxidizing agent employed in the process is preferably in a range from 0.1:1 to 10:1, more preferably from 0.75:1 to 2:1, most preferably 1.0:1.0. In most polymerization reactions the equivalent ratio of catalyst:polymerizable compound employed is from $10^{-12}:1$ to $10^{-1}:1$, more preferably from $10^{-8}:1$ to $10^{-5}:1$.

A beneficial feature of some of the catalysts of this invention, particularly those based on monocyclopentadienyl substituted titanium compounds in combination with an oxidizing agent comprising boron, is that when the catalysts of this invention are used to copolymerize $\alpha$-olefins, either alone or in combination with diolefins, the amount of higher molecular weight olefin or diolefin incorporated into the copolymer is significantly increased when compared to copolymers prepared with the more conventional Ziegler-Natta type catalysts. The relative rates of reaction of ethylene and higher $\alpha$-olefins with the aforementioned titaniumbased catalysts of this invention are so similar that the monomer distribution in copolymers prepared with the catalysts of this invention may be controlled by the ratio of monomeric reactants. Certain of the catalysts are also useful to prepare polymers of vinylaromatic monomers having a high degree of syndiotacticity. Such catalysts have been previously disclosed in copending application Ser. No. 559,475, filed Jul. 30, 1990, and assigned to the same assignee as the present application. The teachings of the above pending application are herein incorporated by reference in their entirety.

"Addition polymerizable monomers" usefully polymerized by catalysts prepared according to the process of the present invention include for example ethylenically unsaturated monomers, acetylenic compounds, conjugated or nonconjugated dienes, polyenes, carbon monoxide, etc. Preferred monomers include the $C_{2-10}$ $\alpha$-olefins especially ethylene, propylene, isobutylene, 1-butene, 1-hexene, 4-methyl-1-pentene, and 1-octene. Other preferred monomers include styrene, $C_{1-4}$ alkyl substituted styrene, tetrafluoroethylene, vinylbenzocyclobutane, ethylidenenorbornene and 1,4-hexadiene.

In general, catalysts prepared by the present process produce polymer products which will be free of certain trace impurities generally found in polymers produced with Ziegler-Natta type catalysts such as aluminum, magnesium, chloride and the like. The polymer products produced with the catalysts of this invention should, then, have a broader range of applications than polymers produced with more conventional Ziegler-Natta type catalysts comprising a metal alkyl such as an aluminum alkyl.

Having described the invention the following examples are provided as further illustration thereof and are not to be construed as limiting. Unless stated to the contrary all parts and percentages are expressed on a weight basis.

EXAMPLE 1

Preparation of Reduced Metal Derivative (($CH_3$)$_4C_5$Si($CH_3$)$_2$N—C($CH_3$)$_3$) Ti(o—$CH_2C_6H_4$N($CH_3$)$_2$) (formula A)

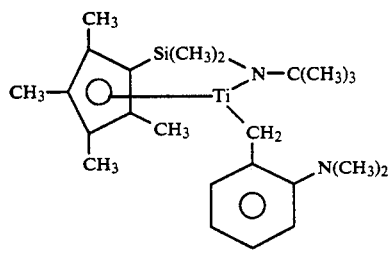

In the drybox, 0.25 g of TiCl$_3$(THF)$_3$ and 0.35 g of (MgCl)$_2$(($CH_3$)$_4C_5$Si ($CH_3$)$_2$N—C($CH_3$)$_3$)(THF)$_2$ were mixed. 15 mL of tetrahydrofuran (THF) was added to give a purple solution. After 5 minutes, 95 mg of o-LiCH$_2C_6H_4$N($CH_3$)$_2$ in 5 mL of THF was added. After 30 minutes, the volatile materials were removed under reduced pressure to yield a red-brown solid. Pentane (20 mL) was added, the solution was filtered, and the volatile materials were removed to give a sticky red-brown solid. This solid was again dissolved in pentane, filtered, and cooled to −45° C. Red crystals were isolated by filtration and dried. The electron paramagnetic resonance (EPR) spectrum of this material exhibited a single line at room temperature (g=1.974) and 2 lines at 77K (consistent with a plane of symmetry in the molecule).

Proper identity of the reduced metal complex was confirmed by also preparing the Ti(IV) chloride of the above complex (Formula B) and analyzing the NMR spectra.

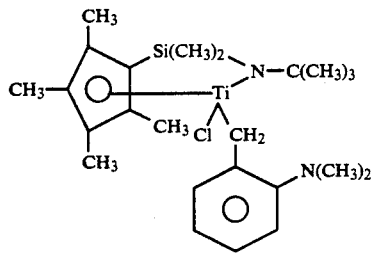

Preparation of catalyst [(($CH_3$)$_4C_5$Si($CH_3$)$_2$N—C($CH_3$)$_3$) Ti(o—$CH_2C_6H_4$N($CH_3$)$_2$)]$^+$ B($C_6F_5$)$^-$ (Formula C)

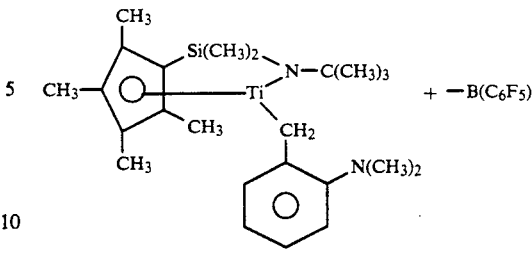

A 50 ml flask was charged with 0.170 g of (($CH_3$)$_4C_5$Si($CH_3$)$_2$N—C($CH_3$)$_3$-)Ti(o—$CH_2C_6H_4$N($CH_3$)$_2$) (0.463 mmol) and 25 ml of toluene. To the resulting red solution 0.280 g (0.382 mmol) of ferrocenium tetrakisperfluorophenyl borate was added as a solid. The solution was stirred for one hour. After this time period the solvent was removed under reduced pressure to give a red oil. The resulting oil was triturated with pentane to give an orange solid. The solid was collected by filtration and washed with toluene (150 ml), dried under reduced pressure to give 0.289 g (69 percent yield) of product. $^1$H NMR (thf-d$_8$) δ7.57-7.65 (m, 4H), 2.71 (s, 3H), 2.33 (bs, 3H), 2.21 (s, 3H), 0.84 (s, 9H), 0.71 (s, 6H).

EXAMPLE 2

Preparation of Reduced Metal Derivative (($CH_3$)$_4C_5$Si($CH_3$)$_2$N—C($CH_3$)$_3$)Ti($C_3H_5$)

In the drybox, 0.30 g of TiCl$_3$(THF)$_3$ and 0.42 g of (MgCl)$_2$(($CH_3$)$_4C_5$Si($CH_3$)$_2$N—C($CH_3$)$_3$)(THF)$_2$ were mixed in a Schlenk tube. 20 mL of THF was added to give a purple solution. The Schlenk tube was sealed and removed to a Schlenk line, and the solution was cooled to −30° C. 0.81 mL of 1.0M allylmagnesiumbromide was added by syringe. After 20 minutes, the solution was warmed to 0° C. and the volatile materials were removed under reduced pressure to yield a dark solid. While keeping the flask at 0° C. pentane (30 mL) was added, and the deep red solution was filtered, concentrated to ca. 5-7 mL, and cooled to −40° C. Red crystals were isolated by filtration and dried in 22 percent yield. The EPR spectrum of this material exhibited a single line at room temperature and 2 lines at 77K (consistent with a plane of symmetry in the molecule). Preparation of catalyst [(($CH_3$)$_4C_5$Si($CH_3$)$_2$N—C($CH_3$)$_3$-)Ti($C_3H_5$)]$^+$B($C_6F_5$)$_4^-$ (Formula D)

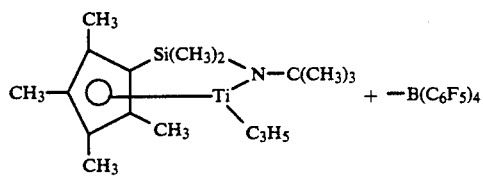

The reaction conditions of Example 1 are substantially repeated using equal molar amounts of the the above reduced metal derivative and ferrocenium tetrakis-perfluorophenyl borate as the anionic oxidizer to cause metal center oxidation.

POLYMERIZATIONS

A 2 L stirred reactor was charged with the desired amounts of mixed alkane solvent (Isopar ™ E, available from Exxon Inc.) and 1-octene comonomer. The reactor was heated to the polymerization temperature and saturated with ethylene at the desired pressure. Hydrogen chain terminator was added by differential pressure expansion from a ~75 mL addition tank. Catalyst were prepared in a drybox by syringing the desired amount of 0.0050M reduced metal derivative solution (in toluene) into a suspension of the solid cationic oxidizer in toluene to provide equal molar ratios of reduced metal derivative and cationic oxidizer. This solution was then transferred to a catalyst addition tank and injected into the reactor. The polymerization was allowed to proceed for the desired time and the solution was removed from the reactor and quenched with hindered phenol anti-oxidant and isopropanol. The polymers were air-dried overnight and then dried in a vacuum oven.

A comparative example was provided utilizing the reduced metal derivative of Examples 1 but using a cationic oxidizer having a coordinating or interfering anion, tetraphenylborate. The comparative polymerization resulted in drastically reduced reaction yield.

Results are contained in Table I.

TABLE I

| Run | Catalyst | Cat. Amt. $\mu$mole | Solvent (ml) | Comonomer (ml) | Ethylene KPa | $\Delta$ H KPa | Temp. °C. | Time (Min.) | Polymer (g) |
|---|---|---|---|---|---|---|---|---|---|
| 1 | Ex. 1 | 10 | 1000 | 200 | 3100 | 340 | 130 | 10 | 192.0 |
| 2 | Ex. 1 | 2.5 | 1150 | 50 | 3400 | 70 | 150 | 10 | 57.8 |
| 3 | Ex. 1 | 1 | 1100 | 100 | 3400 | 70 | 150 | 10 | 55.3 |
| 4 | Ex. 2 | 10 | 1000 | 200 | 3100 | 340 | 130 | 10 | 73.5 |
| 5 | Ex. 2 | 10 | 850 | 350 | 3100 | 170 | 90 | 15 | 228.4 |
| * | 1. | 10 | 1000 | 200 | 3400 | 340 | 130 | 15 | 69.7 |

*comparative
1. $(Me_4C_5SiMe_2N\text{-tert-Bu})Ti(o\text{-}CH_2C_6H_4NMe_2)$ and $[(MeC_5H_4)_2Fe]^+[Ph_4B]^-$

What is claimed is:

1. A process for the preparation of a catalyst useful for addition polymerizations corresponding to the formula:

$$L_lMX_n^+A^-, \text{ wherein:}$$

L independently each occurrence is an anionic or nonanionic ligand or ligand system;

M is a metal of group 4–8 of the periodic table also having an oxidation state, M*, one less than the state of the metal in the catalyst;

X independently each occurrence is hydride; halide; or a group selected from alkyl, alkenyl, silyl, germyl, aryl, and combinations thereof having up to 20 carbon, silicon or germanium atoms, and oxygen, nitrogen, phosphorus or sulfur containing derivatives thereof;

l is an integer greater than or equal to 1;

n is an integer greater than or equal to 1, and the sum of l and n together is one less than the valence of M; and $A^-$ is a monovalent compatible noncoordinating anion, the steps of the process comprising contacting in a noninterfering, noncoordinating solvent at a temperature from $-100°$ C. to $300°$ C. a reduced metal derivative corresponding to the formula: $L_lM^*X_n$, wherein L, l, n, X, and M* are as previously defined with an oxidizing agent capable of oxidizing M* to M and which in reduced form is noninterfering with the resulting catalyst, said oxidizing agent comprising a cationic oxidizer and a compatible noncoordinating anion, $A^-$.

2. A process according to claim 1 wherein the oxidizing agent corresponds to the formula:

$$Ox^+A^-$$

wherein:

$Ox^+$ is a cationic oxidizer capable of oxidizing M* to M; and $A^-$ is a compatible noncoordinating anion.

3. A process according to claim 2 wherein $A^-$ is:

$$[BX_1X_2X_3X_4]^-$$

wherein:

B is boron in a valence state of 3, $X_1$ to $X_4$ are the same or different nonreactive, organyl or silyl radicals containing from 6 to 20 carbon or silicon atoms and optionally two or more of $X_1$ to $X_4$ may be linked to each other through a stable bridging group.

4. A process according to claim 3 wherein $X_1$, $X_2$, $X_3$, and $X_4$ are perfluorinated hydrocarbyl radicals containing from 1 to 20 carbons.

5. A process according to claim 3 wherein $Ox^{+a}$ is ferrocenium, inertly substituted ferrocenium, or $Ag^{+1}$.

6. A process according to claim 1 wherein M is titanium.

7. A process according to claim 1 wherein L is:

a) an anionic ligand selected from the group consisting of, R, $-R'(OR')_mOR$, $(OR')_mOR$, $-PR_2$, $-SR$, $-OR$, $-NR_2$, hydride, and organometalloid radicals comprising a Group 14 element wherein each of the hydrocarbyl substituents contained in the organic portion of said organometalloid, independently, contains from 1 to 20 carbon atoms, wherein R is a hydrocarbyl, silyl, germyl or a substituted hydrocarbyl, silyl, or germyl group of from 1 to 50 carbon, silicon, or germanium atoms;

R' is $C_{2-10}$ alkylene, and m is an integer from zero to ten; or b) a neutral donor ligand selected from the group consisting of, ROR, $NR_3$, $PR_3$, and $SR_2$ wherein R is as above defined.

8. A process according to claim 7 wherein L is a divalent derivative of a substituted cyclopentadienyl group imparting a constrained geometry to the metal active site and containing up to 50 nonhydrogen atoms.

9. A process according to claim 8 wherein L is —Cp*—Z—Y— wherein

Cp* is a cyclopentadienyl or substituted cyclopentadienyl group bound in an $\eta^5$ bonding mode to M;

Z is a divalent moiety comprising oxygen, boron, or a member of group 14 of the periodic table of the elements;

Y is a linking group comprising nitrogen, phosphorus, oxygen or sulfur or optionally Z and Y together form a fused ring system.

10. A process according to claim 1 wherein $L_lM^*X_n$ corresponds to the formula:

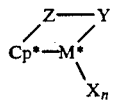

wherein:
$M^*$, and n are as previously defined;
$Cp^*$ is a cyclopentadienyl or substituted cyclopentadienyl group bound in an $\eta^5$ bonding mode to $M^*$;
X is an allyl group or an amino, phosphino or alkoxy substituted hydrocarbyl group of up to 20 carbons;
Z is a divalent moiety comprising oxygen, boron, or a member of group 14 of the periodic table of the elements; and
Y is a linking group comprising nitrogen, phosphorus, oxygen or sulfur or optionally Z and Y together form a fused ring system.

* * * * *

UNITED STATES PATENT AND TRADEMARK OFFICE
CERTIFICATE OF CORRECTION

PATENT NO. : 5,189,192

DATED : February 23, 1993

INVENTOR(S) : Robert E. LaPointe

It is certified that error appears in the above-identified patent and that said Letters Patent is hereby corrected as shown below:

Column 14, line 4, "$\theta^5$" should correctly read --$\eta^5$--.

Signed and Sealed this

Thirtieth Day of November, 1993

Attest:

BRUCE LEHMAN

Attesting Officer

Commissioner of Patents and Trademarks